United States Patent [19]

Sugar et al.

[11] Patent Number: 4,760,019
[45] Date of Patent: Jul. 26, 1988

[54] ANTIGENIC PREPARATION AND DIAGNOSTIC METHOD FOR IDENTIFICATION OF NOCARDIA INFECTIONS

[75] Inventors: Alan M. Sugar, Newton, Mass.; David A. Stevens, Saratoga, Calif.

[73] Assignee: Trustees of Boston University, Boston, Mass.

[21] Appl. No.: 847,997

[22] Filed: Apr. 3, 1986

[51] Int. Cl.$^4$ .................... C12Q 1/28; C01N 33/053
[52] U.S. Cl. ......................................... 435/28; 530/403; 530/350; 436/513; 436/518; 435/7
[58] Field of Search ................ 436/513; 435/28, 518, 435/7; 530/403, 350

[56] References Cited

U.S. PATENT DOCUMENTS 4,613,504  9/1986  Cantrell ................................ 514/2

OTHER PUBLICATIONS

Mauff et al.-Chem. Abst. vol. 96 (1982) p. 213967q.

Primary Examiner—Sam Rosen
Attorney, Agent, or Firm—David Prashker

[57] ABSTRACT

A novel antigenic preparation and unique diagnostic methodology for the detection of human Nocardiosis is provided which is rapid, sensitive, and reproducibly accurate in providing empirical results. The antigenic preparation comprises 55,000 dalton polypeptides derived from an aqueous supernatant fraction of an ammonium sulfate precipitated suspension of Nocardia species cultured in-vitro. The diagnostic methodology utilizes this antigenic preparation in an enzyme immunoassay which is able to distinguish Nocardia infections from persons having Mycobacteria infections and from persons afflicted with other unrelated ailments.

8 Claims, 3 Drawing Sheets

ANTIGENIC PREPARATION AND DIAGNOSTIC METHOD FOR IDENTIFICATION OF NOCARDIA INFECTIONS

FIELD OF THE INVENTION

The present invention is concerned generally with immunological determinants specifically representative of Nocardia species and is specifically directed to diagnostic methods for the identification and detection of nocardiosis in humans.

BACKGROUND OF THE INVENTION

Nocardiosis is an acute or chronic, suppurative disease of humans caused by the soil-inhabiting aerobic mycelial organisms of the genus Nocardia. Although there are more than 40 species in the genus, only a very few are considered infectious and able to cause clinical disease in humans. The infectious species are generally deemed to include: *N asteroides, N. brasiliensis,* and *N. caviae.* There are three distinct clinical syndromes that may evolve from Nocardia infection: primary cutaneous; primary subcutaneous; and primary pulmonary and systemic. The primary cutaneous form of the disease occurs in persons following trauma and contact with soil. Cutaneous infection may present itself as cellulitis, pustules, pyoderma, or a lymphocutaneous form. The primary subcutaneous form of the disease conforms to the clinical entity known as actinomycotic mycetoma causing localized, deforming swollen lesions of suppurating abscesses, granulomata and draining sinuses. The primary pulmonary and systemic forms may be subclinical, pneumonic, chronic, or more rarely acute; the disease may become systemic by hematogenous spread. In this form, the infectious organism has a predilection for the central nervous system and, less commonly, other organs such as the kidney.

Infection with Nocardia species has become more common recently with the ever-increasing use of organ transplants and immunosuppressions associated with the treatment of many diseases [Simpson et al., *Rev. Infect. Dis.* 3:492–507 (1981)]. Clinical diagnosis normally requires the isolation of the causative organism from the subject's tissue or secretions. Unfortunately, this method of diagnosis is very time-consuming and often invasive procedures must be performed in order to secure adequate specimens for clinical evaluation. Some research studies have been attempted to develop a serological test for the diagnosis of nocardiosis; these studies have indicated that there exists a remarkable degree of immunological cross reactivity between tha Nocardia genus and other genera such as Mycobacterium [Kurup, V. P., *Comp. Immunol. Microbiol. Infect. Dis.* 2:69–74 (1979); Shainhouse et al., *J. Clin. Microbiol.* 8:516–519 (1978); Stevens et al., *Am. J. Med.* 71:928–934 (1981); Blumer and Kaufman, *J. Clin. Microbiol.* 10:308–312 (1979)]. Since nocardiosis is a potentially curable disease in humans, it is important that the physician make an accurate and timely diagnosis. Unfortunately, insofar as is presently known, there are no reliable and rapid methods available to meet this challenge. In addition, both epidemiological and clinical research investigations would benefit from the availability of more sensitive and specific methods for the detection of Nocardia based infections.

SUMMARY OF THE INVENTION

The present invention comprises two novel and unique parts: A preparation of immunological determinants specifically representative of Nocardia species comprising a class of homogenous polypeptides recoverable from the aqueous supernatant fraction of an ammonium sulfate precipitated suspension of a Nocardia species cultured in-vitro, these polypeptides being approximately 55,000 daltons in molecular weight. In addition, a diagnostic method is provided for identifying Nocardia infections in human subjects comprising the steps of: obtaining a preparation of immunological determinants comprised of polypeptides recoverable from the aqueous supernatant fraction of an ammonium sulfate precipitated suspension of a Norcardia species cultured in-vitro, said polypeptides being approximately 55,000 daltons in molecular weight; immobilizing these polypeptides onto the surface of a solid substrate; combining a fluid sample derived from the blood of the subject with the immobilized polypeptides as a first reaction mixture; adding a conjugate reactant to the product of this first reaction mixture to form a second reaction mixture, this conjugate reactant comprising an antibody specific for human IgG antibodies and an enzyme which retains at least a portion of its specific activity after being conjugated to the antibody; and adding a chromogenic substrate to the second reaction mixture whereby the formation of an observable colored reaction product identifies the subject as being infected by a Nocardia species.

DETAILED DESCRIPTION OF THE DRAWING

Figure 1:
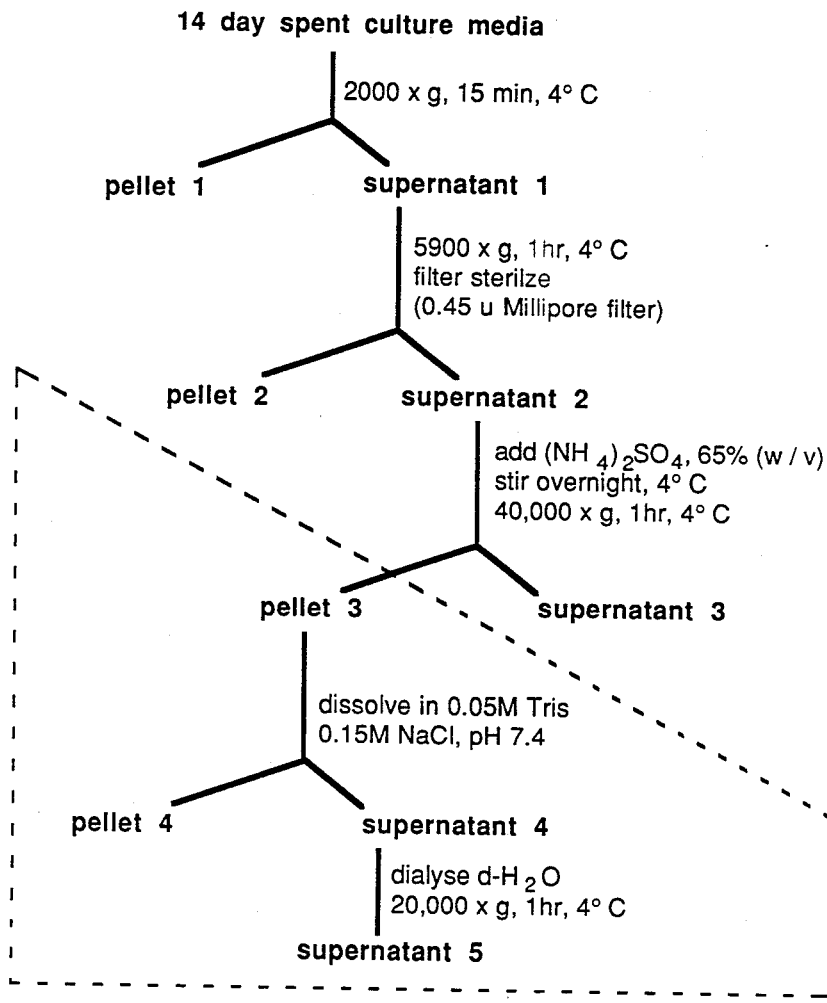

The present invention may be more easily and completely understood when taken in conjunction with the accompanying drawing, in which:

FIG. 1 is a schematic flow diagram of antigenic preparations derived from a culture of *Nocardia asteroides;*

Figure 2:
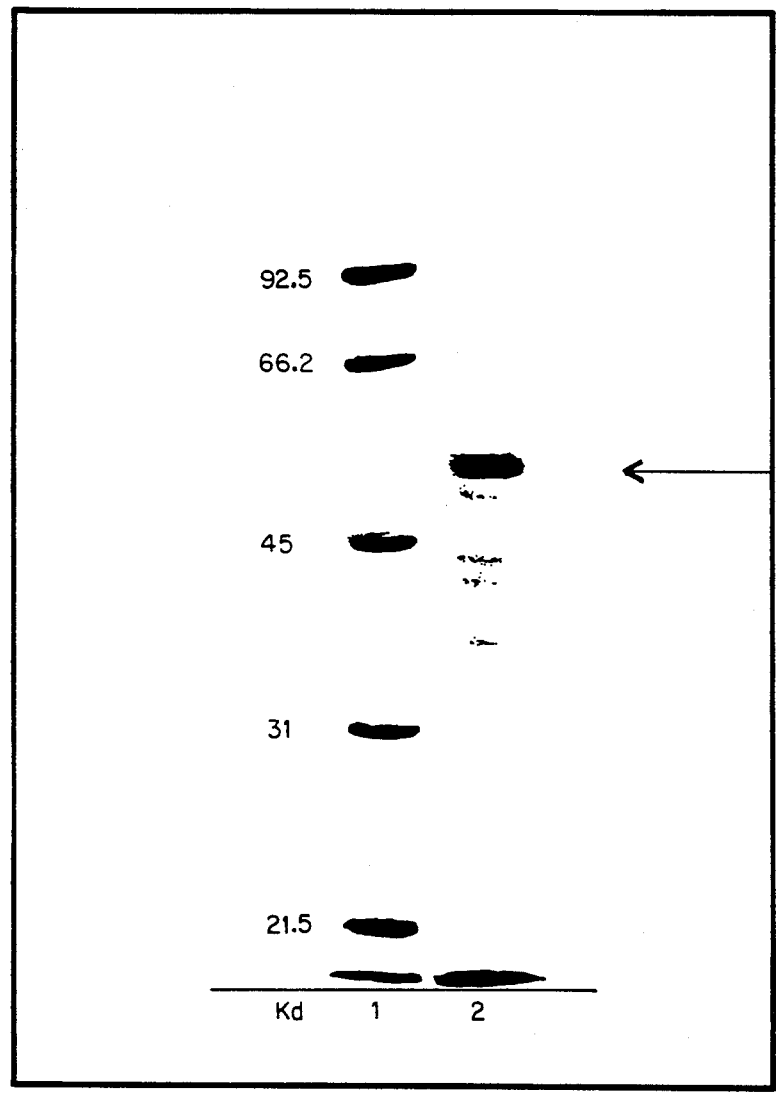
Figure 3:
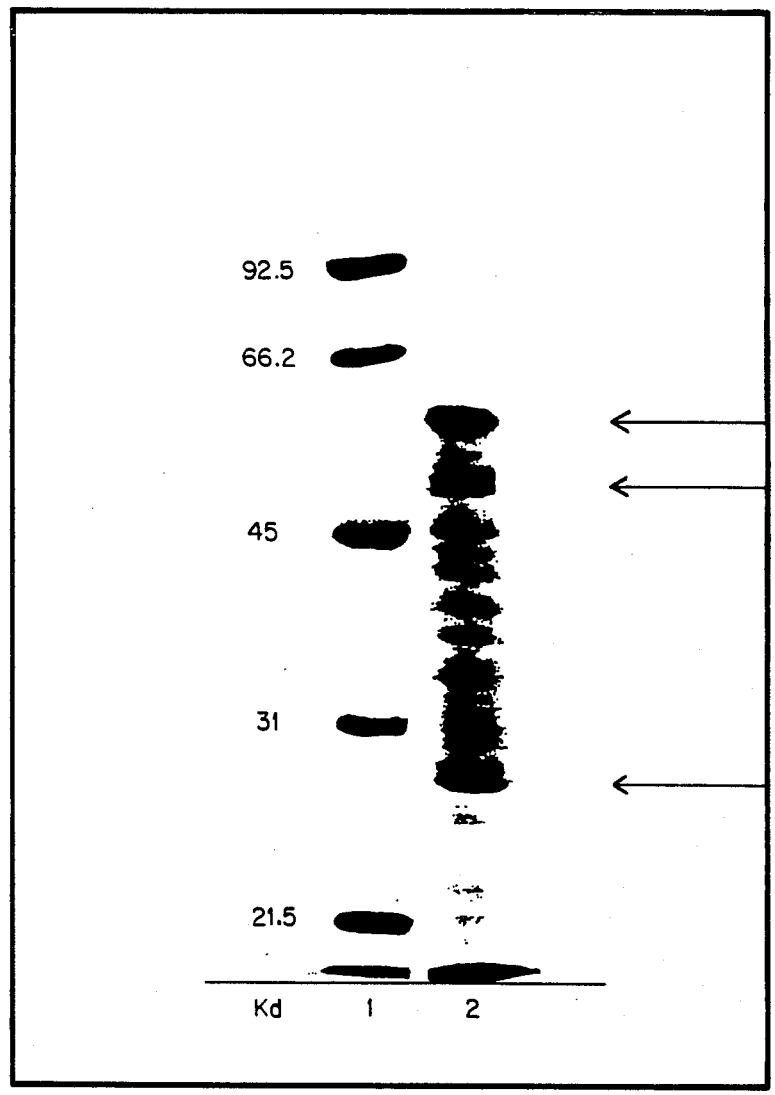

FIG. 2 is an illustration identifying individual polypeptide bands present in the supernatant 3 fraction after polyacrylamide gel electrophoresis and staining with Coomassie blue R-250; and FIG. 3 is an illustration identifying the 25 polypeptide bands comprising the supernatant 5 fraction after polyacrylamide gel electrophoresis and staining with Coomassie blue R-250.

DETAILED DESCRIPTION OF THE PREFERRED EMBODIMENTS

The present invention is a rapid method for clinical diagnosis of human nocardiosis using a 55,000 dalton polypeptide or protein which is recovered from the filtrate of the aqueous supernatant fraction of a Nocardia culture which has been precipitated with ammonium sulfate. This preparation of immunological determinants is specific for and representative of Nocardia species and yields an antigen (or hapten) which specifically binds with such human IgG anti-Nocardia antibodies as may be present in the bloodstream of the patient and is demonstrably non-reactive with antibodies raised against other genera such as Mycobacterium. Once the preparation of immunological determinants has been obtained, the 55,000 dalton polypeptides or proteins predominating in this preparation are chemically immobilized onto the surface of a solid phase or substrate. These immobilized polypeptides are then employed in a conventionally known heterogeneous enzyme immunoassay procedure which employs a conjugate reactant comprising an anti-IgG antibody bound to an enzyme which, in combination with a chromogenic enzyme substrate provides for a colorimetric detection and identification of anti-Nocardia antibodies in a human serum test sample.

The diagnostic methodology for identification and detection of human nocardiosis provides the following advantages not previously available in this art: the methodology employs human serum or plasma-a fluid specimen relatively easy and convenient to obtain from the patient; the test methodology is rapid and accurate; the test methodology may be performed by relatively unskilled technicians without substantial loss of accuracy or precision in the assay; the diagnostic assay is extremely sensitive, antibodies being detected if the serum of some patients even after the serum sample has been diluted to more than 1:4096; and, the diagnostic method is highly reproducible from day to day.

Although the method of preparing the immunodeterminant polypeptides and the diagnostic method respectively are equally useful and applicable to all species within the Nocardia genus, the detailed description will be confined to the use of *N asteroides* with the clear and explicit understanding that this species is merely illustrative and exemplary of all other species within the same genus. On a clinical basis therefore, it will be readily recognized by ordinary practitioners within this art that cultures of *N brasiliensis, N. caviae,* or any other Nocardia species are equally suitable for use. In addition, for purposes of clarity and ease of understanding, the detailed description will be presented in two sections: the preparation of antigenic determinants; and the diagnostic methodology for detection of Nocardia infections in human subjects.

I. Isolation of Specific Immunologicial Determinaets

The organism of choice, *N. asteroides* strain 47N, 7 is a serogroup II isolate which was recovered from an infected human subject [Pier and Fichtner, *J. Clin. Microbiol.* 13:548–553 (1981)]. This strain was grown as a stock culture maintained at −70° C. in 20% glycerol and thawed before use.

To isolate the antigenic determinants, the frozen organisms were thawed and 0.5 milliliter (hereinafter "ml") of this suspension was inoculated into 50 ml of Long's medium (a synthetic chemically defined medium commonly used to grow Mycobacterium) in a 250 ml. Erlenmeyer flask and then incubated for one week at 35° C. on a rotary shaker set at 200 rpm. This provided a starter culture which was rapidly growing.

One ml of this starter culture was then inoculated into 400 ml of Long's medium in a two-liter flask containing a magnetic stir bar. Three flasks were prepared in this manner and incubated at 35° C. with constant stirring for 14 consecutive days. From these organisms cultured in-vitro, two different antigenic preparations were made following the flow diagram of FIG. 1. The preferred preparation is provided by supernatant 3 which provides the immunological determinants in quantities equal to or greater than those of supernatant 5 and in a comparably semi-pure state with far fewer contaminating proteins than is found in supernatant 5. For this reason also, it is the polypeptides which are found in supernatant 3 which are deemed useful as the antigen preparation to be employed for the diagnostic assay for detection of nocardiosis.

Accordingly, according to the flow diagram of FIG. 1, the organisms after growth for 14 days were removed from the media by centrifugation at 2000×gravity for 15 minutes at 4° C. This yielded a pellet 1 which was discarded and a supernatant 1 which was then centrifuged at 5,900×gravity for 1 hour's duration at 4° C. to yield a pellet 2 and a supernatant 2. Pellet 2 was discarded but the clear supernatant 2 was filter sterilized using a 0.45 micron filter (Millipore Corporation). To this filter sterilized supernatant 2 was added sodium azide ($NaN_3$) to a concentration of 0.05% (weight/volume); afterwards, saturated ammonium sulfate was added to supernatant 2 to a final concentration of 65% (weight/volume). This precipitated much of the proteins in the fluid, and this suspension was then centrifuged at 40,000×gravity for 1 hour at 4° C. to yield a precipitate in the form of pellet 3 and a clear supernatant 3 fraction, the preferred source of antigenic determinants.

The supernatant 3 is preferably dialyzed extensively against distilled water using a membrane with a molecular weight cut-off of 12,000–14,000 (Spectrum Medical Industries). The fluid comprising supernatant 3 was then lyophilized in the conventionally known manner and the protein determination made using the method of Lowry et al., [*J. Biol. Chem.* 193:265–275 (1951)] using bovine serum albumin (hereinafter "BSA") as a standard for comparison. It was found that supernatant 3 yields on the average between 5 and 25 micrograms per milliliter (hereinafter "ug/ml") of protein.

To further characterize the nature of the polypeptides comprising the proteinaceous matter of supernatant 3, polyacrylamide gel electrophoresis was performed following the method of Laemmli [*Nature* 227:680–685 (1970)]. A discontinuous buffer system was used with an 8% polyacrylamide-resolving gel and a 4% stacking gel system (12×12 centimeters×0.15 centimeters). The polypeptides were combined with an equal volume of 25% trichloroacetic acid for several minutes and the precipitate was resuspended at 5 times it original concentration in a boiling solution containing 2-mercaptoethanol and 1% sodium dodecylsulfate (hereinafter "SDS"). Approximately 50 microliter (hereinafter "ul") of this solution was applied to the gels. Alternatively, some of the lyophilized preparations were resuspended in boiling water at 5 times their original concentration and then applied to the gels. Electrophoresis was then performed on each sample for approximately 5 hours at 25–30 milliamperes. Subsequently, each of the gels was stained with an aqueous preparation of Coomassie blue R-250 stain. Molecular weight standardards (Bio-Rad Company) were employed to identify the differences in molecular weight between the stained bands in the gels. The results of this analytical procedure to evaluate the polypeptides of supernatant 3 are illustrated by FIG. 2.

Supernatant 3 contains a homogeneous band approximately 55,000 daltons in molecular weight. It is apparent that this 55,000 dalton polypeptide is present in far greater concentration than any other polypeptide in this fraction. In addition, it is noteworthy that there are few polypeptides of other molecular weight present in supernatant 3; in particular, it will be observed that there is no polypeptide band having a 31,000 molecular weight nor is there any proteinaceous band of about 65,000 daltons. Overall therefore, supernatant 3 may properly be said to be primarily composed of polypeptides of 55,000 daltons with relatively few other polypeptides or proteins in this fraction.

The proteinaceous composition comprising supernatant 3 may be directly compared with the proteins and polypeptides comprising the precipitated fraction identified herein as pellet 3. For comparison purposes, the pellet 3 was retained after its original collection by centrifugation and was subsequently dissolved in a solution comprising 0.05 M Tris and 0.15 M NaCl, pH 7.4. This suspension was then centrifuged at 40,000×gravity for one hour at 4° C. to yield a pellet 4 and a supernatant 4 as illustrated in FIG. 1. The supernatant 4 was collected and then dialyzed extensively against distilled water using membrane with a molecular weight cut-off of 12,000–14,000 daltons (Spectrum Medical Industries). After dialysis, the fluid was centrifuged at 20,000×gravity for one hour to remove particulate matter. The fraction identified as supernatant 5 was the result.

Supernatant 5 was then evaluated for its protein content in the earlier described manner for identification of its respective polypeptide constituents. A trichloroacetic acid precipitate of supernatant 5 was resuspended at five times its original concentration in a boiling solution containing 2-mercaptoethanol and 1% SDS. Approximately 50 μl of this preparation was applied to polyacrylamide gels as previously described. In addition, some samples of supernatant 5 were lyophilized and then resuspended in boiling solution at five times their original concentration; these preparations were also subjected to gel electrophoresis in the previously described manner. After electrophoresis, each of the gels were stained with aqueous preparations of Coomassie blue R-250 stain. The results of electrophoretic evaluation of the polypeptides comprising supernatant 5 are illustrated in FIG. 3.

As is seen in FIG. 3, lane 1 demonstrates the individual standard molecular weight markers ranging from 21,500–92,500. Lane 2 identifies the trichloroacetic acid precipitate of supernatant 5 which has been separated into its individual polypeptide constituents as a series of stained bands. It will be appreciated that while the total protein concentration of supernatant 5 was found to be 0.7 mg/ml, this total concentration is represented by approximately 25 individual polypeptide bands ranging from less than 21,500 daltons to more than 92,500 daltons in molecular weight. Equally noteworthy is the presence of three different bands at the molecular weights of approximately 65,000 daltons, 55,000 daltons, and 31,000 daltons which were consistently more heavily stained than any other bands. This heavier staining indicates the greater concentration of these respective polypeptide fractions in comparison to the remaining approximately 22 polypeptide bands comprising supernatant 5 as a whole. Because of their greater concentration in comparison to other polypeptides present within supernatant 5, these three bands were evaluated for their antigenic properties and specificity.

To evaluate the immunological properties of the stained bands comprising 55,000 daltons, and 31,000 daltons respectively, each was combined and reacted with sera from three groups of human patients: sera from human patients with clinical nocardiosis; sera from human patients with clinically diagnosed active tuberculosis; and sera obtained from non-nocardiosis hospitalized human patients or healthy persons. This was achieved in the following manner.

Electrophoretic transfer of the individual bands was achieved following the procedure described by Towbin et al., [Proc. Natl. Acad. Sci. USA 76:4350–4354 (1979)]. The transfer buffer was 50 mM sodium phosphate pH 6.5. Each polypeptide band was transferred from the gel to nitrocellulose paper at 40 V for one hour immediately following completion of gel electrophoresis. The nitrocellulose paper was then dried and 10 or 11 individual strips were cut from each run. One strip was stained with 0.1% amido black and then destained using a solution comprising 40% methanol and 7% acetic acid to confirm protein transfer or developed immunologically as described hereinafter.

The Western blot procedure of Hawks et al. [Anal. Biochem. 119:142–147 (1982)] using 4-chloro-1-naphthol as the colorigenic reagent was followed in all instances. The nitrocellulose strips were first combined for one hour with a solution containing 3% gelatin dissolved in Tris buffered saline (hereinafrer "TBS") containing 20 mM Tris and 500 mM NaCl at pH 7.5. To each nitrocellulose strip was added one of the respective sera under test. All sera were used at 1:20 dilution in TBS plus 1% gelatin and after combination with each strip was allowed to incubate at room temperature for approximately two hours' duration. Subsequently, each reacted strip was washed in a solution comprising TBS and 0.05% Tween 20 to remove all traces of the sera. Afterwards, each strip was combined with a conjugate reactant comprising a goat antibody specific for human IgG antibodies which was conjugated with horseradish peroxidase in a known manner. The conjugate reactant was commercially obtained from Cappel Laboratories (lot number 1412) or from Miles Laboratories (lot number S808). The conjugate reactant was used either at a 1:200 dilution (Cappel) or at a 1:1,000 dilution (Miles) using TBS plus 1% gelatin. Optimal dilutions of the antibodies were determined in a series of preliminary experiments. A final wash using a solution comprising TBS and 0.05% Tween 20 for each nitrocellulose strip was followed by immersion of the respective strips in the colorigenic reagent for between 1–5 minutes. Color development was halted by placing each strip in distilled water for 10 minutes' duration. The results presenting the activity of three different sera with each of the polypeptide bands is given in Table 1 below.

TABLE 1

| Sera | Polypeptide Weight (Daltons) | |
|---|---|---|
| | 55,000 | 31,000 |
| Nocardiosis | 17/17 | 11/17 |
| Tuberculosis | 0/21 | 0/21 |
| Control | 1/25 | 2/25 |

The reactions of 17 different serum samples from patients infected with nocardiosis demonstrated that the 55,000 dalton polypeptide band reacted with all 17 samples; and that the 31,000 dalton band reacted with only 11 samples. Of the 21 serum samples obtained from patients with active tuberculosis, there were no reactions with any of the respective polypeptide fractions. Of the 25 different sera obtained from non-nocardiosis hospitalized patients or healthy persons, only one reacted with 55,000 dalton polypeptides and two reacted with the 31,000 dalton fraction.

On this empirical demonstration of immunological determinants against different kinds of sera, it is seen that only the 55,000 dalton polypeptides have sufficient antigenic specificity (in comparison to their counterparts of different molecular weights) to be deemed adequate and reliable for use as an antigenic preparation in a diagnostic methodology. This is particularly true and proven by the large difference in the reactivity of each polypeptide fraction with sera from patients clinically diagnosed with nocardiosis in which only the 55,000 dalton fraction consistently and repeatedly provided positive results. Accordingly, the 55,000 dalton polypeptides alone comprise the immunological determinants of choice in any diagnostic assay for clinical purposes.

It will be appreciated also that the empirical results demonstrate the desired 55,00 dalton polypeptides to be present in high concentration within the preparation identified herein as supernatant 3. Moreover, because this desired polypeptide predominates over all other proteins within supernatant 3 and because there are comparably few other polypeptides or proteins present within supernatant 3—especially with respect to the approximately 24 other bands identified within supernatant 5—the supernatant 3 fraction is the preparation of choice for the diagnostic methodology.

III. The Preferred Diagnostic Methodology

The antigenic preparation used in this diagnostic assay is the entire fluid fraction designated supernatant 3, prepared as earlier described herein. In its preferred form, supernatant 3 is dialyzsed and lyophilized so that it may be stored until ready for use at −20° C. Since the 55,000 dalton polypeptide is present in this preparation in quantities greater than or equal to any other fraction derived from Nocardia species, and because there were fewer contaminating proteins or polypeptides in the supernatant 3 fraction in comparison to any other derived fraction (supernatant or precipitated pellet), the entire fluid fraction is used as a whole without any further steps at purifying or isolating the specific 55,000 dalton polypeptides alone.

The lyophilized preparation is resuspended in 0.05 M carbonate buffer, pH 9.6 at a preferred protein concentration of 312 ug/ml. 200 ul (approximately 64 micrograms) of this suspension is preferably added to each well of a polystyrene microtiter plate. If desired, the concentration of antigen per microtiter well may be varied from approximately 30-100 ug. Ihis range is expected to meet the majority of requirements encountered in general diagnostic/clinical use. Regardless of the specific concentration employed, the polypeptides in each antigenic dosage will adhere directly to the plastic forming each well of the plate. The optimum antigen concentration may be determined by checkerboard analysis, an evaluation performed by varying the amount of antigen in the wells followed by reacting the contents of each well with a standardized dilution of a positive serum; the optimum antigen concentration is that amount of antigen which produces the highest optical density with the least background reactivity.

After the antigen has been added to each well, the plate is preferably incubated at 4° C. overnight. 1% gelatin dissolved in physiological saline solution (hereinafter "PBS") and 200 ul of this fluid is addad to each well as a blocking agent to reduce non-specific binding between reactants. Subsequently, each well in the plate is washed three times for ten minutes with a wash solution containing 0.85% NaCl and 0.05% Brij 35 (a surfactant). Each well in the plate is now ready to be used in the assay.

For illustratative purposes only, a variety of different test sera was obtained to demonstrate the sensitivity and accuracy of the present diagnostic methodology. For this purpose, sera from 19 human patients clinically diagnosed as being infected with N. asteroides was obtained. Of these, two persons were diagnosed as having cutaneous nocardiosis using conventional methods.

From one patient, N. asteroides was isolated from a halo screw hole in his cranium; was treated for only 10 days with sulfamethoxazole/trimethoprim; and was considered clincially cured when his sera was obtained. The other person had the clinical disease for approximately one month's duration following local trauma to the legs. In addition, one serum sample was taken from a single patient with a seven year history of mycetoma caused by N. brasiliensis. For comparative evaluation, 21 indivldual sera were obtained from human patients clinically afflicted with pulmonary tuberculosis. In addition 82 different control sera were obtained randomly from hospitalized human patients; none of these human patients was known to have been infected with either Nocardia or Mycobacteria species.

For each serum under test, an initial dilution at 1:256 was made in PBS followed by a series of two-fold dilutions in PBS until a final concentration of 1:4096 was obtained. Subsequently, each prepared well in the microtiter plate received 200 ul of the appropriately diluted serum to form a first reaction mixture which was permitted to react for one hour's duration at 37° C. At the end of this incubation period, each well was washed with a 0.85% NaCl solution containing 0.05% Brij 35. Subsequently, the conjugate reactant (goat anti-human IgG bonded to peroxidase) was diluted 1:500 in PBS-Brij and 200 ul of this diluted conjugate reactant was added to each well to form a second reaction mixture. The microtiter plates were then incubated at 37° C. for one hour's duration to yield a reaction product. At that time, each reaction well was rinsed again with the wash solution (0.85% NaCl containing 0.05% Brij 35) and 200 ul of the chromogenic substrate 2,2'-azino-di(3-ethyl benzthazoline) sulfonic acid (hereinafter "ABTS") was added to each well and the reaction allowed to proceed for approximately 15 minutes at room temperature. At that time, the reaction was terminated by adding 0.025 ml of hydrofluoric acid, HF, pH 3.3 to each reaction well. The degree of color development was optically determined at a wavelength of 415 nanometers using an Artek Elisa reader. The results are given in Table 2 below.

TABLE 2

| Sera | Positives/Total Sera |
| --- | --- |
| Nocardiosis | 13/19 |
| Tuberculosis | 0/21 |
| Control | 0/82 |

As Table 2 indicates, none of the 82 individual control sera gave a positive result, that is the occurrence of a visually observable color change in the reaction fluids. Equally notable, none of the 21 individual sera obtained from tuberculosis patients were demonstrably positive that is none provided a colored reaction product as a result of the assay. In contrast, 3 of 19 individual sera (68%) obtained from clinically diagnosed nocardiosis patients gave positive results with individual titers ranging from 1:256 to greater than 1:4096. It should be remembered that the antigenic preparation was made using N. asteroides exclusively. Accordingly, of the six individual sera obtained from nocardiosis patients, it should be noted that: one serum sample was obtained from a person have localized cutaneous disease and thus may have had insufficient antigenic challenge to mount an antibody response; one serum sample was obtained from a person having Nocardia brasiliensis mycetoma which had been on therapeutic medication for an undetermined length of time; and four individual sera samples were obtained from persons diagnosed as having pulmonary nocardiosis. On this basis, therefore, the specificity of the antigen preparation used in this experimental series proves its selectivity to identify positives only in those persons afflicated with *N. asteroides* and only in the type of clinical infection which would lead to the development of specific antibodies in the bloodstream of the infected person. Accordingly, it is deemed that this illustrative experimental series demonstrates a high degree of sensitivity (ability to detect serum in titers of very high dilution) and a high degree of specificity to identify and detect the presence of specific human antibodies raised against a single causative agent.

While the preferred mode of the diagnostic methodology employs commercially obtained anti-human IgG antibodies conjugated to peroxidase enzyme, it will be apparent to ordinary practitioners in the art that this preference is based on convenience, time, and avoidance of the need to prepare one's own reactants in the laboratory. It will be expressly understood however, that a wide variety of different enzymes may be employed for use within the present invention, the preparation of such conjugate reactants being well established and conventionally known in this art. Accordingly, the anti-human Nocardia IgG antibody may be raised against a wide variety of immunogens in a large range of animals; similarly, the enzyme to be bound to the anti-human Nocardia IgG antibody may be selected from any of the many enzymes isolated in the laboratory or commercially available. The exact composition and formulation of the chromogenic substrate to be added thus will vary with the identity and specific activity of the enzyme used in making the conjugated reactant. The choice of anti-human Nocardia IgG antibody, enzyme, and chromogenic substrate employed is thus deemed to be a matter of personal choice or convenience-so long as the following essential requirements are satisfied: it is essential that the anti-human Nocardia IgG antibody be specific for human IgG which is present in the serum sample under test and which is believed to contain anti-Nocardia specificity resulting from clinical infection in a human subject. The enzyme employed must retain a substantial portion of its specific activity after being chemically bound to the anti-human IgG antibody in making the conjugate reactant. The chromogenic substrate should include any and all necessary co-factors or co-enzymes which are necessary for the bound enzyme to produce a colored reaction product.

The present invention is not to be restricted in form nor limited in scope except by the claims appended hereto.

What is claimed is:

1. A proteinaceous antigen specifically representative of Nocardia species comprising:
    a concentration of substantially homogeneous polypeptides having a molecular weight of approximately 55,000 daltons, said polypeptides predominating and being isolatable from an aqueous supernatent fraction obtained by
    growing cells of a Nocardia species in vitro using a culture medium,
    separating said grown Nocardia cells from their culture medium to yield solid matter and an aqueous supernatant fluid,
    combining said fluid with saturated ammonium sulfate to a concentration of about 65% whereby a suspended precipitate is formed, and
    separating said suspended precipitate into solid matter and an aqueous supernatant fraction containing said polypeptides.

2. The antigenic preparation as recited in claim 1 wherein the Nocardia species comprises Nocardia asteroides.

3. The antigenic preparation as recited in claim 1, wherein said Nocardia species is selected from the group consisting of Nocardia brasiliensis and Nocardia caviae.

4. A diagnostic method for identifying Nocardia infections in a human subject comprising the steps of:
    obtaining a proteinaceous antigen specifically representative of Nocardia species comprising a concentration of substantially homogeneous polypeptides having a molecular weight of approximately 55,000 daltons, said polypeptides predominating and being isolatable from an aqueous supernatant fraction obtained by
    growing cells of a Nocardia species in vitro using a culture medium,
    separating said grown Nocardia cells from either culture medium to yield solid matter and an aqueous supernatant fluid,
    combining said fluid with saturated ammonium sulfate to a concentratrion of about 65% whereby a suspended precipitate is formed, and
    separating said suspended precipitate into solid matter and an aqueous supernatent fraction containing said polypeptides;
    immobilizing said polypeptides of said proteinaceous antigen onto the surface of a solid;
    combining a serum sample taken from the subject with said immobilized polypeptides as a first reaction mixture;
    adding a conjugate reactant to said first reaction mixture to form a second reaction mixture, said conjugate reactant comprising an antibody specific for human Nocardia IgG antibodies and an enzyme of specific activity; and
    adding a chromogenic substrate to said enzyme-containing reaction mixture whereby the formation of a colored enzymatic reaction product identifies the subject as being infected by a Nocardia species.

5. The diagnostic method as recited in claim 4 wherein said conjugate reactant comprises goat anti-human IgG antibodies.

6. The diagnostic methods as recited in claim 4 wherein said conjugate reactant comprises horseradish peroxidase.

7. The diagnostic method as recited in claim 4 wherein the chromogenic substrate is 2, 2'-azino-di(3-ethyl benzthazoline) sulfonic acid.

8. The diagnostic method as recited in claim 4 wherein said Nocardia species is at least one selected from the group consisting of N asteroides, N. brasilinensis, and N. caviae.

* * * * *